(12) United States Patent
Yao

(10) Patent No.: US 9,273,326 B2
(45) Date of Patent: Mar. 1, 2016

(54) TETRACYCLINE-REGULATED GENE EXPRESSION IN HSV-1 VECTORS

(75) Inventor: Feng Yao, Needham, MA (US)

(73) Assignee: THE BRIGHAM AND WOMEN'S HOSPITAL, INC., Boston, MA (US)

(*) Notice: Subject to any disclaimer, the term of this patent is extended or adjusted under 35 U.S.C. 154(b) by 2139 days.

(21) Appl. No.: 11/117,375

(22) Filed: Apr. 29, 2005

(65) Prior Publication Data

US 2005/0266564 A1 Dec. 1, 2005

Related U.S. Application Data

(60) Provisional application No. 60/566,594, filed on Apr. 30, 2004.

(51) Int. Cl.
C12N 15/869 (2006.01)
C12N 15/86 (2006.01)

(52) U.S. Cl.
CPC ...... *C12N 15/86* (2013.01); *C12N 2710/16643* (2013.01)

(58) Field of Classification Search
None
See application file for complete search history.

(56) References Cited

U.S. PATENT DOCUMENTS

| | | | |
|---|---|---|---|
| 5,464,758 A * | 11/1995 | Gossen et al. | 435/69.1 |
| 5,589,362 A | 12/1996 | Bujard | |
| 5,917,122 A | 6/1999 | Byrne | |
| 5,965,440 A | 10/1999 | Reeves | |
| 5,972,650 A | 10/1999 | Yao | |
| 6,251,640 B1 | 6/2001 | Yao | |
| 6,261,552 B1 * | 7/2001 | DeLuca | 424/93.2 |
| 6,444,871 B1 * | 9/2002 | Yao | 800/4 |
| 2003/0113348 A1 | 6/2003 | Coffin | |
| 2004/0063094 A1 * | 4/2004 | Coffin et al. | 435/5 |
| 2008/0008686 A1 | 1/2008 | Yao | |
| 2010/0015687 A1 | 1/2010 | Yao | |

FOREIGN PATENT DOCUMENTS

WO   WO 2011/025717 A2   3/2011
WO   WO 2011/079073 A2   6/2011

OTHER PUBLICATIONS

Scaroini et al. Latency associated promoter transgene expression on the central nervous system after sterotaxic delivery of replication-defective HSV-1 based vectors. Gene Therapy, 2001, vol. 8, No. 14, pp. 1057-1071.*
Davido et al. Journal of General Virology, 1996, vol. 77, pp. 1853-1863.*
Schmiesser et al (Human Gene Therapy 13:2113-2124, 2002).*
Yao et al (Human Gene Therapy 9:1939-1950, 1998).*
Berens et al (European Journal of Biochemistry 270:3109-3121, 2003).*
Corbel et al (Current Opinions in Biotechnology 13:448-452, 2002).*
Martinez et al. Journal of Virology 66:6735-6746, 1992.*
Advani, et al., Friendly Fire: Redirecting Herpes Simplex Virus-I for Therapeutic Applications, *Clin. Microbiol. Infect.* 8:551-563 (2002).
Clackson, "Regulated Gene Expression Systems," *Gene Therapy* 7:120-125 (2000).
Deuschle, et al., "Tetracycline-Reversible Silencing of Eukaryotic Promoters," *Mol. Cell. Biol.* 15(4):1907-1914 (1995).
Glorioso, et al., "Therapeutic Gene Transfer to the Nervous System Using Viral Vectors,"*J. Neuro Viral.* 9:165-172 (2003).
Gossen, et al., "Transcriptional Activation by Tetracyclines in Mammalian Cells," *Science* 268:1766-1769 (1995).
Gossen, et al., "Tight Control of Gene Expression in Mammalian Cells by Tetracycline-Responsive Promoters," *Proc. Natl. Acad. Sci. USA* 89:5547-5551 (1992).
Hennighausen, et al., "Conditional Gene Expression in Secretory Tissues and Skin of Transgenic Mice Using the MMTV-LTR and the Tetracycline Responsive System," *J. Cell. Biochem.* 59:463-472 (1995).
Hillen, et al., "Mechanisms Underlying Expression of TN10 Encoded Tetracycline Resistance," *Ann. Rev. Microbiol.* 48:345-369 (1994).
Jacobs, et al., "HSV-1-Based Vectors for Gene Therapy of Neurological Diseases and Brain Tumors: Part I. HSV-1 Structure, Replication and Pathogenesis," *Neoplasia* 1(5):387-401 (1999).
Jacobs, et al., "HSV-1-Based Vectors for Gene Therapy of Neurological Diseases and Brain Tumors: Part II. Vector Systems and Applications," *Neoplasia* 1(5):402-416 (1999).
Kim, et al., "Tetracycline Repressor-Regulated Gene Repression in Recombinant Human Cytomegalovirus," *J. Virol.* 69(4):2565-2573 (1995).
Latchman, et al., "Herpes Simplex Virus Vectors for Gene Delivery to a Variety of Different Cell Types," *Curr. Gene Ther.* 2:415-426 (2002).
Martuza, et al., "Experimental Therapy of Human Glioma by Means of a Genetically Engineered Virus Mutant," *Science* 252:854-856 (1991).
McGeoch, et al., "The Complete DNA Sequence of the Long Unique Region in the Genome of Herpes Simplex Virus Type 1,"*J. Gen. Virol.* 69:1531-1574 (1988).
McGeoch, et al, "Complete DNA Sequence of the Short Repeat Region in the Genome of Herpes Simplex Virus Type 1,"*Nuc. Acids Res.* 14(4):1727-1745 (1986).
McGeoch, et al., "Comparative Sequence Analysis of the Long Repeat Regions and Adjoining Parts of the Long Unique Regions in the Genomes of Herpes Simplex Viruses Types I and 2,"*J. Gen. Virol.* 72:3057-3075 (1991).

(Continued)

*Primary Examiner* — Stacy B Chen
(74) *Attorney, Agent, or Firm* — Nixon Peabody LLP

(57) ABSTRACT

The present invention is directed to HSV-1 vectors which rely on the tetracycline repressor and operator as a means for regulating expression. The vectors utilize VP-16 responsive promoters of HSV to control expression of the tetracycline repressor. The vectors are of particular interest as vehicles for recombinantly expressing genes in vivo.

20 Claims, 1 Drawing Sheet

(56) References Cited

OTHER PUBLICATIONS

No, et al., "Ecdysone-Inducible Gene Expression in Mammalian Cells and Transgenic Mice," *Proc. Natl. Acad. Sci. USA* 93:3346-3351 (1996).
Palmer, et al., "Development and Optimization of Herpes Simplex Virus Vectors for Multiple Long-Term Gene Delivery to the Peripheral Nervous System," *J. Virol.* 74(12):5604-5618 (2000).
Perry, et al., "Characterization of the 1E110 Gene of Herpes Simplex Virus Type 1," *J. Gen. Virol.* 67:2365-2380 (1986).
Postle, et al., "Nucleotide Sequence of the Repressor Gene of the TN10 Tetracycline Resistance Determinant," *Nuc. Acids Res.* 12(12):4849-4863 (1984).
Rivera, et al., "A Humanized System for Pharmacologic Control of Gene Expression," *Nature Medicine* 2(9):1028-1032 (1996).
Wang, et al., "A Regulatory System for Use in Gene Transfer," *Proc. Natl. Acad. Sci. USA* 91:8180-8184 (1994).
Wissman, et al., "Saturation Mutagenesis of the Tn10-Encoded tet Operator $O_1$; Identification of Base-Pairs Involved in Tet Repressor Recognition," *J. Mol. Biol.* 202:397-406 (1988).
Yao, et al., "An Activity Specified by th Osteosarcoma Line U2OS Can Substitute Functionally for ICP0, a Major Regulatory Protein of Herpes Simplex Virus Type 1," *J. Virol.* 69(10):6249-6258 (1995).
Yao, et al., "Tetracycline Repressor, tetR, rather than the tetR-Mammalian Cell Transcription Factor Fusion Derivatives, Regulates Inducible Gene Expression in Mammalian Cells," *Human Gene Ther.* 9:1939-1950 (1998).
Anderson, W.F., "Human Gene Therapy," *Nature (London)* 392:25-30 (1998).
Cohen, J., "Bumps on the Vaccine Road," *Science* 265:1371-1373 (Sep. 1994).
Fox, J.L., "Investigation of Gene Therapy Begins," *Nature Biotechnology* 18:143-144 (Feb. 2000).
Heur, et al., "Tet Repressor-tet Operator Contacts Probed by Operator DNA-modification Interference Studies," *J. Mol. Biol.* 202:407-415 (1988).
Kmiec, et al., "Investigators Have Been Searching for Ways to Add Corrective Genes to Cells Harboring Defective Genes. A Better Strategy Might be to Correct the Defects," *American Scientist* 87:240-247 (May 1999).
Ross, et al., "Gene Therapy in the United States: A Five-Year Status Report," *Human Gene Therapy* 7:1781-1790 (Sep. 1996).
Scarpini, et al., "Latency Associated Promoter Transgene Expression in the Central Nervous System After Stereotaxic Delivery of Replication-Defective HSV-1-Based Vectors," *Gene Therapy* 8:1057-1071 (2001).
Verma, et al., "Gene Therapy-Promises, Problems, and Prospects," *Nature* 389:239-242 (Sep. 1997).
Wang, et at, "Mammary Hyperplasia and Carcinoma in MMTV-Cyclin D1 Transgenic Mice," *Nature* 369:669-671 (Jun. 1994).
Yao, et al., "Physical Interaction Between the Herpes Simplex Virus Type 1 Immediate-Early Regulatory Proteins ICP0 and ICP4," *J. Virol.* 68:8158-8168 (1994).
Yao, et al., "Highly Efficient Regulation of Gene Expression by Tetracycline in a Replication-Defective Herpes Simplex Viral Vector," Mol. *Ther.* 13(4):1133-1141 (Jun. 2006).
Schmeisser, et al., "Tetracycline-Regulated Gene Expression in Replication-Incompetent Herpes Simplex Virus Vectors," *Hum. Gene Ther.* 13:2113-2124 ( Dec. 2002).
Office Action mailed Jan. 26, 2009 in the prosecution of U.S. Appl. No. 11/822,373 along with claims under consideration in the Office Action.
Response to Office Action of Jan. 26, 2009 in the prosecution of U.S. Appl. No. 11/822,373, filed by Applicant on Mar. 31, 2009.
Commmunication re Nonresponsive Amendment mailed in connection with prosecution of U.S. Appl. No. 11/822,373 on Aug. 3, 2009.
Claims pending in U.S. Appl. No. 12/553,051 (division of U.S. Appl. No. 11/822,373), filed Sep. 2, 2009.

Koelle, et al., "Herpes Simplex Virus Infection of Human Fibroblasts and Keratinocytes Inhibits Recognition by Cloned $CD8^{+\ Cytotoxic\ T\ Lymphocytes}$," *J. Clin. Invest.* 91:961-968 (Mar. 1993).
Kousoulas, et al., "Antibody-Resistant Mutations in Cross-Reactive and Type-Specific Epitopes of Herpes Simplex Virus 1 Glycoprotein B Map in Separate Domains," *Virology* 166:423-431 (1988).
Lakeman, et al., "Analysis of DNA From Recurrent Genital Herpes Simplex Virus Isolates by Restriction Endonuclease Digestion," *Sex. Transm. Dis.* 13:61-66 (1986).
Leib, et al, "Immediate-Early Regulatory Gene Mutants Define Different Stages in the Establishment and Reactivation of Herpes Simplex Virus Latency," *J. Virol.* 63(2):759-768 (Feb. 1989).
Lewandowski, et al., "Evidence that deficient IFN-γ production is a biological basis of herpes simplex virus type-2 neurovirulence," *J. Neuroimmunol.* 81:66-75 (1998).
Liesegang, "Herpes Simplex Virus Epidemiology and Ocular importance," *Cornea* 20(1):1-13 (2001).
Looker, et al., "A systematic review of the epidemiology and interaction of herpes simplex virus types 1 and 2," *Sex. Transm. Infect.* 81:103-107 (2005).
Lu, et al., "High Level Expression of Glycoprotein D by a Dominant-Negative HSV-1 Virus Augments its Efficacy as a Vaccine against HSV-1 Infection," *J. Invest. Dermatol.* 129:1174-1184 (2009).
McGeoch, et al., "DNA sequence of the region in the genome of herpes simplex virus type 1 containing the exonuclease and neighbouring genes," *Nucl. Acid Res.* 14(8):3435-48 (1986).
Mertz, et al., "Risk Factors for the Sexual Transmission of Genital Herpes," *Ann. Intern. Med.* 116:197-202 (1992).
Mikloska, et al., "Herpes simplex virus type 1 glycoproteins gB, gC and gD are major targets for CD4 T-lymphocyte cytotoxicity in HLA-DR expressing human epidermal keratinocytes," *J. gen. Virol.* 79:353-361 (1998).
Mikloska, et al., "Monophosphoryl Lipid A and QS21 Increase CD8 T Lymphocyte Cytotoxicity to Herpes Simplex Virus-2 Infected Cell Proteins 4 and 27 Through IFN-1γ and IL-12 Production," *J. Immunol.* 164:5167-5176 (2000).
Minson, et al., "An Analysis of the Biological Properties of Monoclonal Antibodies against Glycoprotein D of Herpes Simplex Virus and Identification of Amino Acid Substitutions that Confer Resistance to Neutralization," *J. gen. Virol.* 67:1001-1013 (1986).
Morrison, et al., "Influence of Mucosal and Parenteral Immunization with a Replication- Defective Mutant of HSV-2 on Immune Responses and Protection from Genital Challenge," *Virology* 243:178-187 (1998).
Muller, "Binding of the Herpes Simplex Virus Immediate-Early Gene Product ICP4 to Its Own Transcription Start Site," *J. Virol.* 61(3):858-865 (Mar. 1987).
Nagot, et al., "Reduction of HIV-1 RNA Levels with Therapy to Suppress Herpes Simplex Virus," *N. Engl. J. Med.* 356(8):790-799 (Feb. 2007).
Para, et al., "Potent Neutralizing Activity Associated with Anti-Glycoprotein D Specificity Among Monoclonal Antibodies Selected for Binding to Herpes Simplex Virions," *J. Virol.* 55(2):483-488 (Aug. 1985).
Pereira, "Use of monoclonal antibodies to HSV-1 and HSV-2 for serological analysis of the viral glycoproteins," *Dev. Biol. Stand.* 52:115-131 (1982).
Pereira, et al., "Type-Common and Type-Specific Monoclonal Antibody to Herpes Simplex Virus Type 1," *Infect. Immun.* 29(2):724-732 (Aug. 1980).
Roberts, et al., "Direct Correlation between a Negative Autoregulatory Response Element at the Cap Site of the Herpes Simplex Virus Type 1 1E175 (α4) Promoter and a Specific Binding Site for the IE175 (ICP4) Protein," *J. Virol.* 62(11):4307-4320 (Nov. 1988).
Roizman, et al., "Herpes Simplex Viruses and Their Replication," Chapter 72, pp. 2399-2459; D.M. Knipe (ed.), Fields Virology, $4^{th}$ ed. Lippincott Williams & Wilkins, Philadelphia, PA. (2001).
Schmidt, et al., "Reinfection is an Uncommon Occurrence in Patients with Symptomatic Recurrent Genital Herpes," *J. Infect. Dis.* 149(4):645-646 (Apr. 1984).
Stanberry, "Clinical Trials of Prophylactic and Therapeutic Herpes Simplex Virus Vaccines," *Herpes* 11(Suppl 3):161A-169A (2004).

(56) References Cited

OTHER PUBLICATIONS

Stanberry, et al., "Prospects for Control of Herpes Simplex Virus Disease through Immunization," *Clin. Infect. Dis.* 30:549-566 (2000).
Stanberry, et al., "Glycoprotein-D-Adjuvant Vaccine to Prevent Genital Herpes," *J. Engl. J. Med.* 347(21):1652-1661 (Nov. 2002).
Starr, et al., "Long-term persistence of defective HSV-1 vectors in the rat brain is demonstrated by reactivation of vector gene expression," *Gene Ther.* 3:615-623 (1996).
Stow, et al., "Isolation and Characterization of a Herpes Simplex Virus Type 1 Mutant Containing a Deletion within the Gene Encoding the Immediate Early Polypeptide Vmw1 10," *J. gen. Viral.* 67:2571-2585 (1986).
Tigges, et al., "Human CD8+Herpes Simplex Virus-Specific Cytotoxic T-Lymphocyte Clones Recognize Diverse Virion Protein Antigens," *J. Virol.* 66(3):1622-1634 (Mar. 1992).
Whitley et al., "Herpes Simplex Viruses," *Clin. Infect. Dis.* 26:541-53; quiz 554-55 (1998).
Xu, et al., "Seroprevalence and Coinfection with Herpes Simplex Virus Type 1 and Type 2 in the United States, 1988-1994," *J. Infect. Dis.* 185:1019-1024 (2002).
Yao, et al., "A Novel Anti-Herpes Simplex Virus Type 1-Specific Herpes Simplex Virus Type 1 Recombinant," *Hum. Gene Ther.* 10:1811-1818 (Jul. 1999).
Yao, et al., "A Novel Tetracycline-Inducible Viral Replication Switch," *Hum. Gene Ther.* 10:419-427 (Feb. 1999).
Yao, et al., "Inhibition of herpes simplex virus type 2 (HSV-2) viral replication by the dominant negative mutant polypeptide of HSV-1 origin binding protein," *Antiviral Res.* 53:127-33 (2002).
Zarling, et al., "Human Cytotoxic T Cell Clones Directed Against Herpes Simplex Virus-Infected Cells," *J. lmmunol.* 136(12):4669-4673 (Jun. 1986).
Abu-Raddad, et al., "Genital Herpes Has Played a More Important Role than Any Other Sexually Transmitted Infection in Driving HIV Prevalence in Africa," *PLoS One* 3(5)(e2230):1-15 (May 2008).
Ackermann, et al., "Characterization of Herpes Simplex Virus 1 α Proteins, 0, 4, and 27 with Monoclonal Antibodies," *J. Virol.* 52(1):108-118 (Oct. 1984).
Adelson, et al., "Simultaneous detection of herpes simplex virus types 1 and 2 by real-time PCR and Pyrosequencing," *J. Clin. Virol.* 33:25-34 (2005).
Akhrameyeva, et al., "Development of a Glycoprotein D-Expressing Dominant-Negative and Replication-Defective Herpes Simplex Virus 2 (IISV-2) Recombinant Viral Vaccine against IISV-2 Infection in Mice," *J. Virol.* 85(10):5036-5047 (May 2011).
Arvin, et al., "Detection of Type-Specific Antibody to Herpes Simplex Virus Type 1 by Radioimmunoassay with Herpes Simples Virus Type 1 Glycoprotein C Purified with Monoclonal Antibody," *Infect. Immun.* 40(1):184-189 (1983).
Augustinova, et al., "The Dominant-Negative Herpes Simplex Virus Type 1 (HSV-1) Recombinant CJ83193 Can Serve as an Effective Vaccine against Wild-Type HSV-1 Infection in Mice," *J. Virol.* 78(11):5756-5765 (Jun. 2004).
Bourne, et al., "DNA immunization confers protective immunity on mice challenged intravaginally with herpes simplex virus type 2," *Vaccine* 14(13):1230-1234 (1996).
Brans, et al., "Prevention of Genital Herpes Simplex Virus Type 1 and 2 Disease in Mice Immunized with gD-Expressing Dominant-Negative Recombinant HSV-1,"*J. Invest. Dermatol.* 129:2470-2479 (2009).
Brans, et al., "Immunization with a Dominant-Negative Recombinant HSV Type 1 Protects against HSV-1 Skin Disease in Guinea Pigs," *J. Invest. Dermatol.* 128:2825-2832 (2008).
Bryson, et al., "Risk of Acquisition of Genital Herpes Simplex Virus Type 2 in Sex Partners of Persons with Genital Herpes: A Prospective Couple Study," *J. Infect. Dis.* 167:942-946 (1993).
Cai, et al., "The Herpes Simplex Virus Type 1 Regulatory Protein ICP0 Enhances Virus Replication during Acute Infection and Reactivation from Latency," *J. Virol.* 67(12):7501-7512 (Dec. 1993).
Cai, et al., "The Herpes Simplex Virus Type 1 'CP0 Plays a Critical Role in the De Novo Synthesis of Infectious Virus following Transfection of Viral DNA," *J. Virol.* 63(11):4579-4589 (Nov. 1989).
Cohen, et al., "Localization and Synthesis of an Antigenic Determinant of Herpes Simplex Virus Glycoprotein D That Stimulates the Production of Neutralizing Antibody," *J. Virol.* 49(1):102-108 (Jan. 1984).
Coleman, et al., "Determination of Herpes Simplex Virus Type-Specific Antibodies by Enzyme-Linked Immunosorbent Assay," *J. Clin. Microbiol.* 18(2):287-291 (Aug. 1983).
Cooper, et al., "Epitope mapping of full-length glycoprotein D from HSV-2 reveals a novel CD4+CTL epitope located at the transmembrane-cytoplasmic junction," *Cell Immunol.* 239:113-120 (2006).
Corey, et al., "Infections With Herpes Simplex Viruses," *N. Eng. J. Med.* 314:749-757 (1986).
Deluca, et al., "Physical and Functional Domains of the Herpes Simplex Virus Transcriptional Regulatory Protein ICP4," *J. Virol.* 62(3):732-743 (Mar. 1988).
Dolan, et al., "The Genome Sequence of Herpes Simplex Virus Type 2," *J. Virol.* 72(3):2010-2021 (Mar. 1998).
Dudek, et al., "Replication-defective viruses as vaccines and vaccine vectors," *Virology* 344:230-239 (2006).
Fleming, et al., "Herpes Simplex Virus Type 2 in the United States, 1976 to 1994," *N. Eng. J. Med.* 337(16):1105-1111 (1997).
Freeman, et al., "Herpes simplex virus 2 infection increases HIV acquisition in men and women: systematic review and meta-analysis of longitudinal studies," *Aids* 20:73-83 (2006).
Glorioso, et al., "Immunogenicity of Herpes Simplex Virus Glycoproteins gC and gB and Their Role in Protective Immunity," *J. Virol.* 50(3):805-812 (Jun. 1984).
Grammer, et al., "Identification of an HSV-1/HSV-2 Cross-Reactive T Cell Determinant," *J. Immunol.* 145(7):2249-2253 (Oct. 1990).
Gupta, et al., "Genital Herpes," *Lancet* 370:2127-2137 (Dec. 2007).
Handler, et al., "Oligometric Structure of Glycoproteins in Herpes Simplex Virus Type 1," *J. Virol.* 70(9):6067-6075 (Sep. 1996).
Hirsch, "Herpes Simplex Virus," p. 1144-1153. In G.L. Mandell, R.G.J. Douglas and J.E. Bennett (ed.), Principles and practice of infectious diseases. Churchill Livingstone Inc., New York (1990).
Honess, et al., "Type Specific and Type Common Antigens in Cells Infected with Herpes Simplex Virus Type 1 and on the Surfaces of Naked and Enveloped Particles of the Virus," *J. gen. Virol.* 22:159-169 (1974).
Hosken, et al., "Diversity of the CD8+T-Cell Response to Herpes Simplex Virus Type 2 Proteins among Persons with Genital Herpes," *J. Virol.* 80(11):5509-5515 (Jun. 2006).
Johnson, et al., "Herpes Simplex Virus Glycoprotein D is Recognized as Antigen by CD4+ and CD8+T Lymphocytes from Infected Mice," *J. Immunol.* 145(2):702-710 (Jul. 1990).
Jones, et al., "Vaccination Strategies to Prevent Genital Herpes and Neonatal Herpes Simplex Virus (HSV) Disease," *Herpes* 11(1):12-17 (2004).
Kim, et al., "Immunodominant Epitopes in Herpes Simplex Virus Type 2 Glycoprotein D Are Recognized by CD4 Lymphocytes from Both HSV-1 and HSV-2 Seropositive Subjects," *J. Immunol.* 181:6604-6615 (2008).
Knopf, et al., "Evaluation of the T-REx™ transcription switch for conditional expression and regulation of HSV-1 vectors," *Virus Genes* 36:55-66 (2008).
Koelle, et al., "Herpes Simplex: Insights on Pathogenesis and Possible Vaccines," *Annu. Rev. Med.* 59:381-395 (2008).
Koelle, et al., "Recent Progress in Herpes Simplex Virus Immunobiology and Vaccine Research," *Clin. Microbiol. Rev.* 16(1):96-113 (Jan. 2003).
Koelle, et al., "Prospects for Developing an Effective Vaccine Against Ocular Herpes Simplex Virus Infection," *Curr. Eye Res.* 30:929-942 (2005).

\* cited by examiner

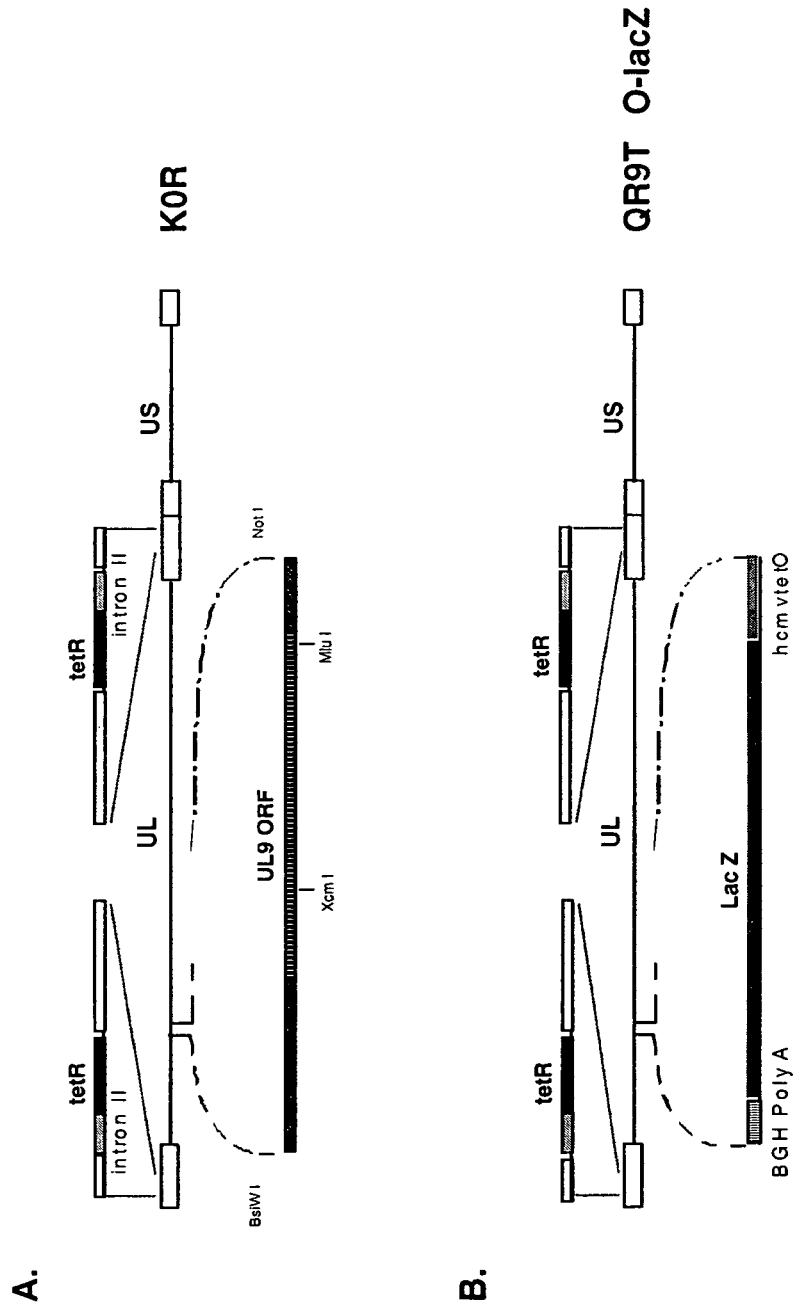

TETRACYCLINE-REGULATED GENE EXPRESSION IN HSV-1 VECTORS

CROSS REFERENCE TO RELATED APPLICATIONS

The present application claims the benefit of U.S. provisional application No. 60/566,594 filed on Apr. 30, 2004, which is incorporated in its entirety herein by reference.

GOVERNMENT SUPPORT

This invention was made with Government support under Grant Numbers AI050880 and GM051449 awarded by the National Institutes of Health. The Government has certain rights in this invention.

FIELD OF THE INVENTION

The present invention is concerned with HSV-1 vectors in which gene expression is controlled using the tetracycline operator and repressor. Expression of sequences coding for the tetracycline repressor is under the control of HSV-1 immediate-early promoters. Because gene expression from HSV-1 immediate-early promoters is significantly enhanced by the HSV-1 virion-associated transactivator VP-16 upon the entry of virus into a host cell, a very high level of repressor expression occurs at the time of infection. As a result, gene expression from promoters under the control of tetracycline operator sequences is essentially completely suppressed. Upon exposure of cells to tetracycline, repressor is released from the operator sequence and gene expression proceeds. Using this system, very high levels of expression can be obtained in neurons in vivo and this expression can be closely regulated.

BACKGROUND OF THE INVENTION

Herpes simplex virus type 1 (HSV-1) is a linear double stranded DNA virus with genome size of about 152 kb. The genome of HSV-1 is encapsided by an icosadeltarhedral capsid surrounded by a viral envelope. HSV replicates in epithelial cells and establishes life-long latent infection in neuronal cell bodies within the sensory ganglia of infected individuals. The latent viral genome is maintained in an episomal state and does not ordinarily cause serious disease or interfere with normal cellular function (Rock, et al., *J. Virol.* 55:849-852 (1985)). These characteristics have made HSV of particular interest for use as a vehicle for gene therapy procedures designed to treat diseases of the CNS (Latchman, *Curr. Gene Ther.* 2:415-426 (2002); Glorioso, et al, *J. Neurovirol.* 9:165-172 (2003); Jacobs, et al., *Neoplasia* 1:402-416 (1999); Advani, et al., *Clin. Microbiol. Infect.* 8:551-563 (2002); Martuza, et al., *Science* 252:854-856 (1991)). One difficulty that has been associated with the development of such procedures has been in finding vectors that induce high expression levels of delivered genes and do so in a manner that can be tightly regulated.

During the past decade, significant progress has been made in developing genetic switches that can be used to control the expression of recombinantly delivered genes (Clackson, *Gene Ther.* 7:120-125 (2000); Gossen, et al., *Proc. Nat'l Acad. Sci. USA* 89:5547-5551 (1992); Gossen, et al., *Science* 268:1766-1769 (1995); No, *Proc. Nat'l Acad. Sci USA* 93:3346-3351 (1996); Wang, et al., *Proc. Nat'l Acad. Sci. USA* 91:8180-8184 (1994); Rivera, et al., *Nat. Med.* 2:1028-1032 (1996)). In the case of prokaryotic elements associated with the tetracycline (tet) operon, systems have been developed in which the tet repressor protein is fused with polypeptides known to modulate transcription in mammalian cells. The fusion protein has then been directed to specific sites by the positioning of the tet operator sequence. For example, the tet repressor has been fused to the activation domain of transactivator (VP-16) and targeted to tet operator sequences positioned upstream from the TATA element of promoter of a selected gene (Gossen, et al., *Proc. Natl. Acad. Sci. USA* 89:5547-5551 (1992); Kim, et al., *J. Virol.* 69:2565-2573 (1995); Hennighausen, et al., *J. Cell. Biochem.* 59:463-473 (1995)). The tet repressor portion of the fusion protein binds to the operator thereby transporting the VP-16 activator to the specific site where the induction of transcription is desired. An alternative approach has been to fuse the tet repressor to the KRAB repressor domain and target this protein to an operator placed several hundred base pairs upstream of a gene. Using this system, it has been found that the chimeric protein, but not the tet repressor alone, is capable of producing a 10 to 15-fold suppression of CMV regulated gene expression (Deuschele, et al., *Mol. Cell Biol.* 15:1907-1914 (1995)). One problem with these types of systems is that a portion of fusion proteins corresponding to the mammalian transactivator or repressor trends to interact with cellular transcription factors and cause pleiotropic effects.

Recently, a tetracycline-inducible transcription switch for use in mammalian cells was developed (U.S. Pat. No. 6,444, 871; Yao, et al., *Hum. Gene Ther.* 9:1939-1950 (1998)). This system was highly successful at regulating gene expression and has been used in developing plasmid-based vectors that are now sold commercially (T-REx™, Invitrogen, CA).

SUMMARY OF THE INVENTION

The present invention is concerned with HSV-1 vectors that can be used for recombinantly expressing a structural sequence in vivo. HSV-1 vectors are recognized in the art as being made up of three components: a capsid, a viral envelope, and genomic DNA. The present invention is particularly concerned with the genomic DNA but it will be understood that the other components which make up the vectors, i.e., the HSV capsid and viral envelope are also present. The term "structural sequence" as used herein refers to a sequence of nucleotides encoding either a polypeptide or an RNA segment, particularly an antisense RNA segment, that is not translated into protein.

More specifically, the invention is directed to a recombinant HSV viral vector containing a genomic DNA construct that includes at least two (and preferably only two) nucleotide sequences coding for tetR, each of which is under the regulation of an VP-16 responsive HSV-1 immediate-early promoter. This promoter may be the HSV-1 ICP-0 or ICP-4 immediate early promoter or a hybrid formed by combining these promoters with the HSV-1 latency-associated promoter LAP2. To make a hybrid promoter between ICP0 and LAP2 (ICP0/LAP2) or between ICP4 and LAP2 (ICP4/LAP2), a DNA fragment containing the LAP2 promoter (Palmer et al., *J Virol* 74:5604-5618 (2000)) is inserted at about 250-500 bp upstream of (i.e., 5' to) the TATA element of the ICP0 or ICP4 promoter.

The genomic DNA construct carried by the HSV-1 vector also includes an additional promoter that is characterized by the presence of a TATA element. A tetracycline operator sequence (tetO) is positioned so that the first nucleotide in tetO is between 6 and 24 nucleotides 3' to the last nucleotide in the TATA element (i.e., counting the first nucleotide 3' to the TATA element as "1," the first nucleotide in the tetO sequence would be nucleotide "6"-"24." Lying 3' to the tetO sequence is the structural sequence and this is operably linked to the additional promoter, i.e., expression of the structural sequence is under the control of the additional promoter.

The tetO sequence occurs in different forms depending upon the presence or absence of two well recognized tetR binding sites designated as Op-1 and Op-2. The most preferred form of operator for use in the present invention has two Op-2 sites, each such site having the nucleotide sequence: CCCTATCAGTGATAGAG (SEQ ID NO:1). In a preferred embodiment, these two Op-2 sites are joined by a linker sequence 3-10 nucleotides in length, with a linker of four nucleotides being most preferred.

In other preferred embodiments, the additional promoter present in the DNA vector described above is the human cytomegalovirus (hCMV) immediate early promoter or the LAP2/hCMV immediate-early promoter. However, other strong promoters may also be used. In one embodiment, the structural gene whose expression is regulated by the second promoter is LacZ. This gene serves as a marker that can be used for identifying infected cells that are actively expressing genes recombinantly. Methods for producing such vectors and using them to study gene expression in vitro and in vivo are described in detail in the Examples section below.

The HSV-1 vectors described above should, most typically, be replication deficient. The term "replication deficient" as used herein means that the genomic DNA of the virus has been engineered so that it cannot replicate when injected into a subject. As described further in the Examples section, one way of producing a replication-deficient HSV-1 vector is to modify its genome so that it is no longer capable of expressing a functional UL-9 gene. Under these circumstances, vector will only replicate if the UL-9 gene product is provided, e.g., during in vitro culture.

The genomic DNA constructs can be made using standard methods for synthesizing and splicing DNA. Alternatively, viral DNA can be directly altered so that either an endogenous ICP-0 gene or an endogenous ICP-4 gene has been replaced with a sequence coding for the tetracycline repressor. The replacement must occur in such a fashion that tetR is operably linked to either the ICP-0 or ICP-4 promoter and the tetR protein is correctly produced. The virus must also contain at least one recombinant structural sequence located 3' to a tetO sequence and which is operably linked to an additional promoter. The additional promoter must have a TATA element and the tetO segment must begin 6-24 nucleotides 3' to the last nucleotide in the TATA element.

Finally, the invention includes methods for recombinantly expressing selected nucleotide sequences in host cells by infecting them with the HSV-1 vectors described above. The selected nucleotide sequence should be present in the virus as the "recombinant structural sequence." The method is particularly well adapted for obtaining recombinant expression in neurons in vivo. This will provide a means for scientists to determine how on- and off or dose-dependent expression of a variety of recombinant genes affects neuronal growth and development. Infection may also be performed on host cells in vitro which may then be transplanted into an animal or studied directly.

BRIEF DESCRIPTION OF THE DRAWINGS

FIG. 1: Schematic diagram of genomes of HSV-1 recombinants KOR (A) and QR9TO-lacZ (B): UL and US represent the unique long and unique short regions of the HSV-1 genome, respectively, which are flanked by their corresponding inverted repeat regions (open boxes). Replacements of the ICP0 coding sequences in both repeats surrounding UL region with DNA elements encoding tetR (black box) and intron II of the rabbit β-globin gene (obliquely striped box) flanked by ICP0 sequences are shown above the diagram of the HSV-1 genome. An expanded map of the region of UL9 containing the UL9 open reading frame (black line box) and flanking sequences between restriction sites BsiW I and Not I is shown below the diagram. Relevant restriction sites within the UL9 open-reading frame used to construct QR9TO-lacZ are indicated. (B) QR9TO-lacZ was generated by replacing the Xcm I-Mlu I DNA fragment within the UL9-coding sequences of KOR with DNA sequences containing lacZ gene (gray box) under control of the tetO-bearing hCMV major immediate-early promoter (cross hatched box). The line box shows the polyadenylation signal sequence of bovine growth hormone gene.

DEFINITIONS

The description that follows uses a number of terms that refer to recombinant DNA technology. In order to provide a clear and consistent understanding of the invention, including the scope to be given to terms, the following definitions are provided:

DNA genomic construct: As used herein, the term "DNA genomic construct" refers to the DNA that is carried by recombinant HSV-1 and which contains a variety of elements that allow for the expression of a structural sequence after the DNA is introduced into a host cell. The expression of the structural sequence is under the control of (i.e., operably linked to) regulatory sequences such as promoters or enhancers. Unless otherwise indicated, promoters may be constitutive, inducible or repressible.

Vector: The term "vector" or "viral vector" is the system for expressing a recombinant DNA sequence in a host cell. As used herein, it refers to a DNA genomic construct-containing HSV viral recombinant which can introduced said genomic construct into a host cell.

Expression: Expression is the process by which a polypeptide is produced from DNA. The process involves the transcription of a gene into mRNA and the translation of this mRNA into a polypeptide. Depending on the context in which it is used, "expression" may refer not only to the expression of polypeptide, but also to the production of RNA, particularly antisense RNA.

Promoter: A promoter is a DNA sequence that initiates the transcription of a gene. Promoters are typically found 5' to the gene and located proximal to the start codon. If a promoter is of the inducible type, then the rate of transcription increases in response to an inducing agent.

Host cell: A host cell is the recipient of a DNA vector. Host cells may exist either in vivo or in vitro.

Recombinant: As used herein, the term "recombinant" refers to nucleic acid that is formed by experimentally recombining nucleic acid sequences and sequence elements. A recombinant host cell would be a cell that has received recombinant nucleic acid.

Operably linked: The term "operably linked" refers to genetic elements that are joined in such a manner that enables them to carry out their normal functions. For example, a gene is operably linked to a promoter when its transcription is under the control of the promoter and such transcription produces the protein normally encoded by the gene.

Structural sequence: As used herein, the term "structural sequence" refers to a sequence of nucleotides that undergoes transcription. Structural sequences may either encode a polypeptide or an antisense RNA sequence.

DETAILED DESCRIPTION OF THE INVENTION

The present invention is directed to HSV-1 vectors that can be used to express recombinant sequences in neuronal cells, especially in vivo. Expression is regulated using the tetracycline operator and repressor protein (for sequences see Postle et al., *Nucl. Acid Res.* 12:4849-4863 (1984); Hillen et al., *Ann. Rev. Microbiol.* 48:345-369 (1994); Wissmann et al., *J. Mol. Biol.* 202:397-406 (1988)). General methods for making vectors containing these elements have been previously described (see U.S. Pat. No. 6,444,871) and plasmids which contain the tetracycline-inducible transcription switch are commercially available (T-REx™, Invitrogen, CA). The essential features are the presence of a structural sequence (e.g., a gene sequence that one wants to be expressed in a host cell) which is operably linked to a promoter that has a TATA element. A tet operator sequence is located between 6 and 24 nucleotides 3' to the last nucleotide in the TATA element of the promoter and 5' to the structural sequence. When DNA with these characteristics is present in a cell that also expresses the tetracycline repressor, transcription of the structural gene will be blocked by the repressor binding to the operator. If tetracycline is introduced however, it will bind to the repressor, cause it to dissociate from the operator, and transcription of the structural gene will proceed.

The HSV-1 vectors also include at least two sequences coding for the tetracycline repressor and expression of each of these sequences is under the control of either an ICP-0 or ICP-4 immediate early promoter of HSV-1. The sequences for the ICP-0 and ICP-4 promoters and for the genes whose regulation they endogenously control are well known in the art (Perry, et al., *J. Gen. Virol.* 67:2365-2380 (1986); McGeoch et al., *J. Gen. Virol.* 72:3057-3075 (1991); McGeoch et al., *Nucl. Acid Res.* 14:1727-1745 (1986)) and procedures for making vectors containing these elements are described in detail in the Examples section below. These promoters are not only very active in promoting gene expression, they are also specifically induced by VP16 a transactivator that is released when HSV-1 infects a cell. Thus, transcription from ICP-0 or ICP-4 is particularly high when repressor is most needed to shut down transcription of the structural sequence.

Vectors having the characteristics described above can be produced using standard methods of molecular biology and DNA synthesis. However, it is also possible to produce an appropriate vector by modifying the wild type HSV-1 genome. Specifically, the ICP-0 or ICP-4 genes may be deleted from the viral genome and replaced with a structural sequence in a manner that puts it under the control of the ICP-0 or ICP-4 promoter. Since the HSV-1 genome contains more than one ICP-0 or ICP-4 gene, more than one repressor element will be included in a vector. In the most preferred embodiment, two sequences coding for tet repressor are present. This provides a greater concentration of repressor for binding to the tetracycline operator and shutting off transcription.

The strength with which the tet repressor binds to the operator sequence is, preferably, enhanced by using a form of operator which contains two Op-2 repressor binding sites linked by a sequence of approximately four nucleotides. When repressor is bound to this operator, essentially no transcription of the structural sequence will occur. Many different promoters may be used for controlling the expression of the structural sequence. Examples include the mouse metallothionein I promoter (Hamer, et al., *J. Mol. Appl. Gen.* 1:273-288 (1982)); herpes virus promoters (Yao et al., *J. Virol.* 69:6249-6258 (1995); McKnight, *Cell* 31:355-365 (1982)); the SV40 early promoter (Benoist, et al., *Nature* 290:304-310 (1981)); and, especially, the human CMV immediate-early promoter (Boshart, et al. *Cell* 41; 521-530 (1985)) or LAP2/hCMV immediate-early promoter (Palmer et al., J Virol 74:5604-5618 (2000)).

Once appropriate genomic DNA constructs have been produced, they may be incorporated into HSV-1 viral recombinants using methods that are well known in the art. The most preferred procedure is described in the Examples section, but other methods are also compatible with the present invention. It is preferred that the virus be replication deficient, i.e., incapable of replicating once it is introduced in vivo. Any method for producing a replication deficient virus known in the art may be used. In the case of HSV-1 the most preferred procedure is to either delete or mutate the viral UL-9 gene so that it no longer makes functional protein (for UL-9 sequence, see McGeoch, et al., *J. Gen. Virol.* 69:1531-1574 (1988)). Again, procedures for carrying this out are described in the Examples section and in references provided herein.

The structural sequence in HSV vectors can encode any protein or RNA sequence that one wants to express in a host cell. For example, HSV vectors in which the structural sequence codes for a marker such as LacZ may be used to study the ability of HSV-1 or another virus to deliver genes to cells in vivo and the extent to which the structural sequence is expressed after delivery. This type of evaluation is very important in the development of methods that can be used in gene therapy. Other genes, e.g., genes coding for growth factors, antisense sequences, cytokines or therapeutic agents, may also be used as the structural sequence and delivered to cells. The ability to turn on and off expression after delivery by administering or withholding tetracycline provides scientists with a way to study the effect of the expressed sequence on cell biology. It also provides a way for evaluating the therapeutic potential of a vector. For example, by studying factors that contribute to neuronal growth and development, procedures may be developed that can be used to help promote nerve regeneration in patients where tissue has been destroyed due to stroke or traumatic injury. Similarly, neoplastically transformed neurons can be targeted with vectors producing agents such as interferons or other therapeutic agents to determine whether there is an effect on tumor growth or metastasis. In addition CNS diseases such as Alzheimer's disease, Parkinson's disease, ALS, multiple sclerosis and Huntington's disease may also be studied and potential therapies for these diseases tested.

EXAMPLES

In the present example, a tetracycline-inducible transcription switch is introduced into a novel replication-defective HSV-1 vector, QR9TO-lacZ. Infection of cells with QR9TO-lacZ can achieve a 1000-fold increase in regulated gene expression by tetracycline in mammalian cells. The demonstrated ability of QR9TO-lacZ to deliver very high levels of sensitively regulated gene expression significantly expands the utility of HSV-based vector systems for the study of protein function in the nervous system and their potential in human gene therapy applications.

A. Materials and Methods

Plasmids: pSH is an ICP0-expressing plasmid with flanking sequences 957 bp upstream of the ICP0 open-reading frame to 415 bp downstream of the ICP0 translation stop codon (Cai, et al., *J. Virol.* 63:4579-4589 (1989)). pSH-tetR is a tetracycline repressor-expressing plasmid in which expression of tetR is under the control of the HSV-1 ICP0 promoter. It was generated by replacing the Nco I-Sal I ICP0 coding sequence-containing fragment in plasmid pSH with the Kpn I-Sal I tetR-containing fragment of pGEM-tetR (Yao, et al., Hum. Gene Ther. 9:1939-1950 (1998)). Nco I linearized pSH was blunt-ended with mung bean nuclease to remove the initiation codon, ATG, of the ICP0 open-reading frame while the Kpn I-linearized pGEM-tetR was blunt-ended by T4 DNA polymerase treatment. The HSV-1 UL9-expressing plasmid, pcDNAUL9, was constructed by inserting the BsiW I-Not I UL9-containing fragment of pL9 (Baradaran, et al., J. Virol 68:4251-4261 (1994)) into pcDNA3 at the Nru I and Not I sites. pcDNAUL9 expresses UL9 from the HSV-1 UL9 promoter with the bovine growth hormone (BGH) polyadenylation signal sequence at its 3' end. Plasmid p9DNATO-lacZ, which contains the lac Z gene under control of the tetO-bearing hCMV major immediate-early promoter with the BGH poly A signal at the 3' end of the lac Z gene, was generated by replacing the Xcm I-Mlu I fragment containing UL9 amino acids 217 to 803 in plasmid pUL9-V, with DNA sequences consisting of the tetO-hCMV-lacZ-poly A transcription unit (see FIG. 1) pUL9-V is a derivative of pcDNAUL9 with a deletion of a 17-bp Not I-Xba I fragment present in pcDNA3.

Cells: African green monkey kidney (Vero) cells and osteosarcoma cells, U2OS, were grown and maintained in Dulbecco's modified Eagle's medium (DMEM) supplemented with 10% fetal bovine serum (Yao, et al., J. Virol. 69:6249-6258 (1995)). U2OS cells express a cellular activity that can substitute functionally for the HSV-1 immediate-early regulatory protein, ICP0 (Yao, et al., J. Virol. 69:6249-6258 (1995)). U2CEP4R11 cells, a tetR-expressing cell line derived from U2OS cells, were grown and maintained in the above-mentioned growth medium in the presence of hygromycin-B at 50 µg/ml (Yao, et al., Hum. Gene Ther. 9:1939-1950 (1998)).

RUL9-8 is a double-stable cell line expressing both tetR and UL9, which was established by stable transfection of U2CEP4R11 cells with pcDNAUL9 using procedures described previously (Yao, et al., Hum. Gene Ther. 9:1939-1950 (1998)). These cells can support the growth of an HSV-1 UL9 insertion mutant hr94 efficiently.

Rat pheochromocytoma (PC12) cells were grown and maintained in DMEM supplemented with 10% heat-inactivated horse serum (Invitrogen) and 5% heat-inactivated fetal bovine serum. For differentiation of PC12 cells, cells were seeded in PC12 cell differentiation medium (DMEM supplemented with 2% heat-inactivated horse serum and 1% heat-inactivated fetal bovine serum containing 50 ng/ml of 2.5 S NGF (Upstate Biotechnologies)) at $2 \times 10^5$ cells per dish on 60-mm culture dishes coated with collagen I for one week followed by treatment with medium containing 20 µM fluorodeoxyuridine (Sigma) to remove undifferentiated PC12 cells (Su, et al., J. Virol. 73:4171-4180 (1999)). Cells were maintained in PC 12 cell-differentiation medium for an additional 2 days prior to infection.

Viruses: The ICP0 null mutant 7134, in which both copies of the ICP0 coding sequence have been replaced by the Lac Z gene of Escherichia coli (Cai, et al., J. Virol 63:4579-4589 (1989) was propagated and assayed in U2OS cells (Yao, et al., J. Virol. 69: 6249-6258 (1995)). Infectious 7134 DNA was isolated from purified 7134 virions according to procedures previously described ((Yao, et al., J. Virol. 69:6249-6258 (1995)).

KOR is an HSV-1 recombinant in which the Lac Z genes of 7134 were replaced by homologous recombination with a DNA fragment containing tetR in pSH-tetR. In brief, U2OS cells were co-transfected with the linearized pSH-tetR plasmid and infectious HSV-1 7134 DNA using lipofectin (Yao, et al., Hum. Gene Ther. 9:1939-1950 (1998)). Progeny of the transfection were screened by standard plaque assay in the presence of 5-bromo-4-chloro-3-indolyl-β-D-galactoside (X-Gal) at 96 h post-infection (Yao, et al., Hum. Gene Ther. 10:1811-1818 (1999)). White plaques contain virus in which both copies of the Lac Z gene are replaced by the tetR DNA. These were isolated following four rounds of plaque purification to yield KOR. The expression of tetR in KOR was verified by Western blot analysis of cell extracts prepared from mock-infected U2OS cells and from U2OS cells infected with either 7134 or KOR. The tetR-specific monoclonal antibody used was purchased from Clontech, Palo Alto, Calif.

Infection and β-galactosidase Assay: Vero and PC12 cells were seeded at $1 \times 10^6$ cells per 60-mm dish. At 48 h post-seeding, Vero cells were mock-infected or infected with either 3 PFU/cell or 10 PFU/cell of QR9TO-lacZ. For PC12 cells, infections were carried out at 120 h post-seeding with either 1 or 3 PFU/cell. Infections were performed in the absence or presence of tetracycline. Mock-infected and infected cell extracts were prepared for β-galactosidase assays according the protocol described by Invitrogen (Carlsbad, Calif.). Protein concentrations in cell extracts were determined by the Pierce BCA protein assay (Pierce Biotechnology, Rockford, Ill.). β-galactosidase activity was expressed as nmoles of ONPG hydrolyzed/min/mg protein (Invitrogen). For visible X-Gal staining, at various times post-infection, cells were washed with PBS, fixed with 0.05% glutaraldehyde, and stained with X-Gal at 500 µg/ml in PBS solution containing 5 mM potassium ferricyanide and 5 mM potassium ferrocyanide.

Mice: Female CD-1 mice six to eight weeks of age were purchased from Taconic Laboratory (Germantown, N.Y.). Mice were housed in metal cages at four mice per cage and maintained on a 12-h light/dark cycle. Mice were allowed to acclimatize for one week prior to experimentation. Mice were randomly assigned to several different groups and fed with either a normal diet or a diet containing tetracycline at 6 g/kg (Bio-Serv, Frenchtown, N.J.). After 7 days of feeding, mice were anesthetized with sodium pentobarbital and inoculated either intracerebrally with 20 µl of QR9TO-lacZ into the left frontal lobe of the brain at a depth of 2.5 mm or by subcutaneous inoculation into hindlimb footpads. Mice were fed ad libitum with either a normal diet or a tetracycline-containing diet. Control mice were inoculated with DMEM. Mouse brains or footpads were harvested on days 1, 2, or 3 post-inoculation. After tissues were fixed in 4% paraformaldehyde for 2 h, they were washed with PBS and stained with X-Gal for 3 h at 37° C.

B. Results

Construction of the T-REx™-containing Single Replication-defective HSV-1 Vector:

To generate a replication-defective HSV-1 recombinant encoding the newly developed tetR-mediated repression switch, we first constructed a tetR-expressing HSV-1 recombinant, KOR, by replacing both copies of the HSV-1 ICP0 open-reading frame with DNA sequences encoding tetR (FIG. 1A). Second, to replace the essential UL9 gene of HSV-1 in KOR (FIG. 1A) with the Lac Z gene under control of the tetO-bearing hCMV major immediate-early promoter, we transfected UL9-expressing RUL9-8 cells with linearized p9DNATO-LacZ DNA followed by KOR super-infection. Progeny virus was plaque assayed on RUL9-8 cell monolayers in the presence of tetracycline and X-Gal. Blue plaques, indicating that the UL9 gene had been replaced by the lacZ gene, were isolated and plaque purified four times. QR9TO-lacZ (FIG. 1B) is a viral recombinant that exhibits strong X-Gal staining in infected Vero or U20S cells in the presence of tetracycline but little or no staining in the absence of tetracycline, indicating that the expression of Lac Z gene can be effectively controlled by tetracycline in cells infected with QR9TO-lacZ.

The replication-defective nature of QR9TO-lacZ was confirmed by plaque assays on RUL9-8, U20S, and Vero cell monolayers. The plaque-forming efficiency of QR9TO-lacZ on ICP0-complementing U20S cell monolayers was reduced more than $5 \times 10^6$-fold compared with that in RUL9-8 cells. When assayed on non-ICP0 complementing Vero cell monolayers, the plaque-forming ability of QR9TO-lacZ was reduced to less than $1.14 \times 10^{-8}$ PFU/ml. Given that the plaque-forming efficiency of an ICP0 null mutant on Vero cell monolayers is reduced by more than 100-fold relative to U20S cell monolayers, the titer of QR9TO-lacZ on Vero monolayers is less than $5 \times 10^{-8}$ PFU/ml.

Quantitative analysis of tetracycline-regulated $\beta$-gal expression in QR9TO-lacZ-infected cells: To assess the efficiency of QR9TO-lacZ in delivering tetracycline-regulatable gene expression in mammalian cells, we compared the levels of lacZ expression following QR9TO-lacZ infection in both the presence and absence of tetracycline by quantitative $\beta$-galactosidase ($\beta$-gal) analysis. Compared with cells infected in the absence of tetracycline, levels of Lac Z expression in QR9TO-lacZ-infected cells in the presence of tetracycline were increased by 1024-fold and 541-fold at MOIs of 3 and 10 PFU/cell respectively.

An examination of tetracycline-dose-dependent regulation of $\beta$-gal expression in QR9TO-lacZ infected Vero cells, showed that levels of $\beta$-gal expression in QR9TO-lacZ infected cells can be finely adjusted by varying the dose of tetracycline. Maximum $\beta$-gal expression was detected at a tetracycline concentration of 0.5 µg/ml, which was 966-fold higher than that detected in QR9TO-lacZ-infected Vero cells in the absence of tetracycline.

Taken together, these results demonstrate that QR9TO-lacZ, a T-REx™ encoding replication-defective HSV-1 viral recombinant, is capable of delivering robust and tightly regulated gene expression to mammalian cells.

Regulation of $\beta$-gal expression in QR9TO-lacZ-infected un-differentiated and NGF-differentiated PC12 cells: In an effort to evaluate its potential application as an efficient vector for delivering regulated gene expression to neural cells, we next infected both undifferentiated and 2.5 S NGF-differentiated PC12 cells with QR9TO-lacZ in the absence and presence of tetracycline. The X-Gal staining experiments showed that, whereas very few X-Gal positive staining cells were detected in undifferentiated and NGF-differentiated PC12 cells infected with QR9TO-lacZ in the absence of tetracycline, close to 50% of undifferentiated and differentiated PC12 cells infected with QR9TO-lacZ exhibited strong X-Gal staining in the presence of tetracycline. No blue cells were observed in mock-infected cells. In addition, on the basis of the similarity of both cell density and morphology between infected cells and mock-infected controls, the study indicated that QR9TO-lacZ exhibits little cytotoxicity in infected, undifferentiated and NGF-differentiated PC 12 cells.

A quantitative analysis of $\beta$-gal expression in undifferentiated and NGF-differentiated PC 12 cells was performed after infection with QR9TO-lacZ in the absence or presence of tetracycline. It was found that a 200-fold or greater increase in tetracycline dependent induction of $\beta$-gal expression was achieved under the experimental conditions described. Infection of PC12 cells with QR9TO-lacZ at an MOI of 3 PFU/cell yielded a 669-fold increase in $\beta$-gal expression by tetracycline. The specific-$\beta$-gal activity detected in tetracycline treated QR9TO-lacZ-infected differentiated PC 12 cells at an MOI of 10 PFU/cell was nearly 300-fold higher than that detected in the absence of tetracycline.

Tetracycline-regulated $\beta$-gal expression in vivo: CD-1 mice were fed standard food or tetracycline-containing food one week prior to inoculation of the left frontal lobe or the hindlimb footpads with QR9TO-lacZ. X-Gal staining was examined in the brains of mice on days 1, 2, and 3 after inoculation of the left lobe. Direct in vivo delivery of QR9TO-lacZ led to strong X-Gal staining of tissue along the needle tract in brains of mice fed tetracycline. No X-Gal specific staining was detected in brains of mice fed standard food.

X-Gal staining was also examined in footpad tissues (n=6) of mice 48 h post-infection. For each mouse footpad, sagittal or transverse sections were cut at a thickness of 8 µm per section and every sixth section was examined for the presence of X-Gal staining. Large numbers of X-Gal positive staining cells were detected in QR9TO-lacZ-infected footpad tissues of tetracycline-treated mice. We did, however, observe a few X-Gal positive cells in footpad tissues of mice that were not fed tetracycline. These cells exhibited a staining intensity much lower than that observed in footpad tissue prepared from tetracycline-fed mice. The average number of X-Gal-positive cells from a total of 23 sections per footpad was: 0 in the mock-infected group, 6.67±6.121 in the absence of tetracycline and 813.33±777.79 in the presence of tetracycline.

C. Discussion

The hCMV major immediate-early enhancer-promoter is one of the most potent and promiscuous cis-regulatory elements used for enhancing expression of transgenes in both in vitro and in vivo. By inserting the tetracycline operator such that the first nucleotide is positioned 10 bp downstream of the last nucleotide of the TATATAA element (TATA element) of the hCMV major immediate-early promoter, we have shown that the tetracycline repressor (tetR) can act as a potent repressor to down-regulate gene expression from the tet operator-bearing hCMV major immediate-early promoter. It was shown that gene expression from the tetracycline operator-bearing hCMV major immediate-early enhancer-promoter can be regulated by tetR over three orders of magnitude in response to tetracycline, whereas in the absence of tetR, the tetO-bearing hCMV major immediate-early enhancer-promoter exhibits the same promoter activity as the wild-type promoter.

In the present example, two specific strategies were used for introducing the tet-On gene switch into a replication-defective HSV-1 vector. First, based on the fact that the efficacy of T-REx™ in achieving regulation of gene expression is influenced by the levels of tetR within cells and that the HSV-1 immediate-early ICP0 promoter is one of the strongest HSV-1 immediate-early promoters whose activity is significantly enhanced by the virion-associated transactivator VP16, we constructed an HSV-1 recombinant, KOR, encoding two copies of the tetR gene by replacing the ICP0 gene with DNA encoding tetR under control of the ICP0 promoter. This design allows high level of expression of tetR upon virus entry into the cell. Second, given that a combination of the deletion of ICP0 gene with the blockage of HSV-1 viral DNA replication by the dominant-negative HSV-1 UL9 origin binding protein, UL9-C535C, significantly reduces the cytotoxicity of the resulting recombinant as compared with HSV-1 recombinants with a deletion in genes encoding ICP4 or ICP27, we replaced the essential UL9 gene in KOR with DNA encoding the Lac Z gene under control of the tetO-containing hCMV major immediate-early promoter, which renders the resulting recombinant, QR9TO-lacZ, replication-defective in non-UL9 complementing cells. Notably, since QR9TO-lacZ is propagated in non-ICP0-transformed ICP0-complementing UL9-expressing cells, there should be no concern about potential generation of a viral recombinant that contains the wild-type ICP0 gene, which plays a major role in enhancing reactivation of latent HSV.

Analysis of QR9TO-lacZ infection of Vero cells, PC12 cells, and NGF-differentiated PC12 cells revealed a 300- to 1000-fold enhancement in gene expression by tetracycline in these cells. We also showed that expression of the lac Z gene in QR9TO-lacZ-infected cells can be controlled by tetracycline in a dose-dependent manner. This highly efficient means of regulating gene expression can also be achieved in vivo following intracerebral and footpad inoculations in mice, demonstrating its potential utility for regulating gene expression in gene therapy applications and analysis of gene function in the nervous system.

Although available evidence indicates that long-term gene expression can be achieved with the hCMV major immediate-early promoter in replication-defective HSV-1 vectors following intra-articular delivery in rabbits and injection into inguinal adipose tissue in mice, gene expression from the hCMV-immediate-early promoter is generally suppressed in latently infected neurons following HSV vector-mediated gene transfer. This shortcoming can, however, be overcome with the use of the LAP2/hCMV immediate-early promoter, a hybrid promoter between the HSV-1 latency-associated promoter LAP2 and the hCMV major immediate-early promoter. It has been demonstrated that HSV-1 recombinants containing the LAP2/hCMV immediate-early promoter can yield efficient long-term transgene expression in latently infected neurons (Palmer, et al., *J. Virol.* 74:5604-5618 (2000)). Thus, for achieving potential long-term regulatable gene delivery to the CNS, a QR9TO-lacZ-like HSV vector could be constructed, in which the expression of a target gene is controlled by the tetO-bearing LAP2/hCMV immediate-early promoter, while the tetR gene is under control of the LAP2/hCMV immediate-early promoter, or a hybrid promoter between LAP2 and an HSV-1 immediate-early promoter.

All references cited herein are fully incorporated by reference. Having now fully described the invention, it will be understood by those of skill in the art that the invention may be practiced within a wide and equivalent range of conditions, parameters and the like, without affecting the spirit or scope of the invention or any embodiment thereof.

What is claimed is:

1. A replication deficient HSV-1 viral vector having a genomic DNA construct comprising:
   a) at least two tetR nucleotide sequences coding for the tetracycline repressor, wherein the expression of each tetR nucleotide sequence is under the control of a VP-16 responsive immediate early promoter selected from the group consisting of: the ICP-0 immediate early promoter of HSV-1; the ICP-4 immediate early promoter of HSV-1; LAP2/ICP0; and LAP2/ICP4;
   b) an additional promoter wherein said additional promoter includes a TATA element;
   c) a tetracycline operator sequence positioned between 6 and 24 nucleotides 3' to said TATA element; and
   d) a structural sequence whose expression is regulated by said additional promoter
   and wherein
      i) said viral vector does not include a functional ICP-0 gene and;
      ii) said viral vector releases VP-16 that promotes tetR gene expression from said VP-16 responsive immediate early promoter at the time said viral vector infects a cell.

2. The HSV-1 vector of claim 1, wherein said VP-16 responsive immediate early promoter is either the ICP-0 immediate early promoter of HSV-1 or the ICP-4 immediate early promoter of HSV-1.

3. The HSV-1 vector of claim 1, wherein said VP-16 responsive immediate early promoter is either LAP2/ICP0 or LAP2/ICP4.

4. The HSV-1 vector of claim 1, wherein said genomic DNA construct has only two tetR sequences.

5. The HSV-1 vector of claim 1, wherein said tetracycline operator contains two Op2 sites, each site having the sequence CCCTATCAGTGATAGAG (SEQ ID NO:1).

6. The HSV-1 vector of claim 5, wherein said two Op2 sites are joined by a linker sequence 3-10 nucleotides in length.

7. The HSV-1 vector of claim 1, wherein said additional promoter is the LAP2/hCMV immediate-early promoter.

8. The vector of claim 1, wherein said structural sequence encodes LacZ.

9. The vector of claim 1, wherein said structural sequence codes for a therapeutic agent.

10. The HSV-1 vector of claim 1, wherein said HSV-1 vector is replication deficient due to the absence of a functional UL-9 gene in said genomic DNA construct.

11. The HSV-1 vector of claim 1, wherein said tetR nucleotide sequences have replaced endogenous HSV-1 sequences coding for ICP-0.

12. The HSV-1 vector of claim 11, wherein said genomic DNA construct has only two tetR sequences.

13. The HSV-1 vector of claim 11, wherein said tetracycline operator contains two Op2 sites, each site having the sequence CCCTATCAGTGATAGAG (SEQ ID NO:1).

14. The HSV-1 vector of claim 13, wherein said two Op2 sites are joined by a linker sequence 3-10 nucleotides in length.

15. The HSV-1 vector of claim 14, wherein said structural sequence codes for a therapeutic agent.

16. The HSV-1 vector of claim 10, wherein said tetR nucleotide sequences have replaced endogenous HSV-1 sequences coding for ICP-0.

17. The HSV-1 vector of claim 16, wherein said genomic DNA construct has only two tetR sequences.

18. The HSV-1 vector of claim 16, wherein said tetracycline operator contains two Op2 sites, each site having the sequence CCCTATCAGTGATAGAG (SEQ ID NO:1).

19. The HSV-1 vector of claim 18, wherein said two Op2 sites are joined by a linker sequence 3-10 nucleotides in length.

20. The HSV-1 vector of claim 19, wherein said structural sequence codes for a therapeutic agent.

* * * * *

SEQUENCE LISTING

<160> NUMBER OF SEQ ID NOS: 1

<210> SEQ ID NO 1
<211> LENGTH: 17
<212> TYPE: DNA
<213> ORGANISM: Escherichia coli

<400> SEQUENCE: 1
ccctatcagt gatagag                                              17